(12) United States Patent
Jordan et al.

(10) Patent No.: US 6,476,003 B1
(45) Date of Patent: Nov. 5, 2002

(54) METHOD FOR PREPARING SMALL PARTICLE SIZE GLUCAN IN A DRY MATERIAL

(75) Inventors: Frank M. Jordan, Reno, NV (US); Ruth A. Gault, Reno, NV (US); Kenneth W. Hunter, Reno, NV (US)

(73) Assignee: Immusonic, Inc., Carson City, NV (US)

( * ) Notice: Subject to any disclaimer, the term of this patent is extended or adjusted under 35 U.S.C. 154(b) by 106 days.

(21) Appl. No.: 09/707,583

(22) Filed: Nov. 6, 2000

(51) Int. Cl.⁷ .......................... C07H 1/08; A61K 31/175
(52) U.S. Cl. .................... 514/54; 536/123.12
(58) Field of Search ..................... 536/123.12; 514/54

(56) References Cited

U.S. PATENT DOCUMENTS

| | | | |
|---|---|---|---|
| 4,891,220 A | 1/1990 | Donzis | 424/88 |
| 5,223,491 A | 6/1993 | Donzis | 514/54 |
| 5,397,773 A | 3/1995 | Donzis | 514/54 |
| 5,508,191 A * | 4/1996 | Kanegae et al. | 435/252.2 |
| 5,519,009 A | 5/1996 | Donzis | 514/54 |
| 5,576,015 A | 11/1996 | Donzis | 424/442 |
| 5,705,184 A | 1/1998 | Donzis | 424/442 |
| 5,738,852 A | 4/1998 | Robinson et al. | 424/199.1 |
| 5,858,776 A | 1/1999 | Ostrand-Rosenberg et al. | 435/325 |
| 5,861,310 A | 1/1999 | Freeman | 435/325 |

OTHER PUBLICATIONS

Greenfeild EA, Nguyen KA, Kuchroo VK. CD28/B7 costimulation: a review. Crit Rev Immunol 1998;18(5):389–418.

Harris NL, Ronchese F. The role of B7 costimulation in T–cell immunity. Immunol Cell Biol Aug.1999: 77(4):304–11.

\* cited by examiner

Primary Examiner—Peter O'Sullivan
(74) Attorney, Agent, or Firm—The Matthews Firm

(57) ABSTRACT

An improved method for purifying glucan to small particle size glucan and drying the glucan to a solid such that the glucan may be re-hydrated and maintain substantially maintain a particle size of one micron or less so that it may be used in nutritional, pharmaceutical and pharmacological compositions where a dry material is desired such that a greater immunological benefit may be obtained.

19 Claims, 5 Drawing Sheets

|  | LPS<br>n=54 | Starting Glucan<br>n=55 | Sonicated Glucan<br>n=56 | Media<br>n=50 |
|---|---|---|---|---|
| Average # bio-particles per cell | 1.75 | 2.92 | 3.00 | 3.04 |
| # Cells ingesting bio-particles | 24 | 23 | 31 | 15 |
| # Cells without bio-particles | 30 | 32 | 25 | 35 |
| % Phagocytosis | 44.44% | 41.82% | 55.36% | 30.00% |

*FIG. 4*

|  | LPS<br>(50 μg/ml) | Glucan Globules<br>(100 μg/ml) | Sonicated Globules<br>(100 μg/ml) | Media |
|---|---|---|---|---|
| TNF-α (pg/ml) | 573 | 153 | 144 | 0 |
| NO (μM) | >1000 | 275 | 600 | 0 |

*FIG. 5*

METHOD FOR PREPARING SMALL PARTICLE SIZE GLUCAN IN A DRY MATERIAL

RELATED APPLICATIONS

This application is related to an application entitled "Improved Method for Preparing Small Particle Size Glucan" and an application entitled "Improved Method for Preparing Small Particle Size Glucan in a Finely Dispersed Powder" filed on the same day as the present application.

TECHNICAL FIELD

The present invention relates generally to an improved method for the preparation of small particle size glucan in a dry material. More particularly, the present invention relates to the preparation of small particle size glucans in a dry material that modulate immunological activity in humans and animals.

BACKGROUND ART

Glucans are polymers of glucose. Glucans are commonly found in the cell walls of bacteria, yeast, and various plant species. A common glucan is beta (1,3)-linked glucopyranose (commonly referred to as beta glucan). Other common examples include mixtures of beta-(1,3)-linked glucopyranose with beta-(1,6)-linked glucopyranose. These glucans have been shown to have immunopharmacological activity in humans and animals. More particularly, beta (1,3) glucan has been shown to effect some immune responses.

The prior art does contain methods of preparation of a glucan containing composition, but not a stable small particle size glucan containing composition.

For example, U.S. Pat. No. 5,576,015 to Donzis discloses the use of a beta glucan as both a nutritional and topological agent. The '015 patent discloses that beta (1,3) glucan may be combined with a suitable pharmaceutical carrier for topical application to the skin. Further, the '015 patent discloses that beta (1,3) glucan may be administered orally. As well, the '015 patent discloses that a small particle size glucan is preferred to a glucan product which comprises larger sized glucan particles. However, the '015 patent does not explain why the small particle size is desirable nor whether a small particle size glucan is necessary or even how to achieve and maintain the small particle size glucan.

A preferred size of the glucan particle disclosed in the '015 patent is one micron in diameter. Accordingly, the '015 patent discloses that a beta glucan may be more immunologically effective the smaller the particle size of the beta glucan. However, the method of grinding beta glucan disclosed by Donzis does not effectively produce a consistent small particle size beta glucan. Additionally, no matter to what size the grinding reduces the glucan, the glucan containing composition prepared by the '015 patent re-aggregates into a large particle size glucan upon hydration. Accordingly, the '015 patent does not disclose a reliable method of producing a fine grind beta glucan in which the particle size of a glucan is predominantly one micron or less.

Various methods exist in the prior art for the production of glucan containing compositions. However, only soluble glucan has been created in a substantially purified form to date. Methods of producing insoluble glucan produce glucan containing compositions in which the glucan is not in a substantially purified form. A general method for the production of glucan containing compositions from yeast involves extraction with alkali followed by extraction with acid. This method is considered to be extremely time consuming and labor intensive and was described in detail in 1991 in an article published in Carbohydrate Research. (Nicholas R. Di Luzio et al., "A method of solubilization of a (1–3)-B-D-glucan isolated from Saccharomyces cerevisiae," 219 Carbohydrate Research, 203–213 (1991).

Another more modem method is disclosed in U.S. Pat. No. 5,223,491 to Donzis. The improved method of Donzis discloses a primary difference from that of previous preparation methods in that yeast material is first autoclaved in an alkali solution, followed by an acid extraction and ethanol wash. The patent states the method produces a particularly potent insoluble glucan product which is substantially free of protein and non-glucose sugars, and which significantly stimulates the activities of macrophages. However, studies conducted on the product of the '491 patent indicate that the product was substantially more protein than glucan. Further, the method of the '491 patent allows the glucan to re-aggregate upon re-hydration to an aggregate size of greater than one micron in diameter. As the glucan re-aggregates to a size of greater than one micron in diameter, some of the beneficial effect of the glucan is not achieved because the macrophage receptors are not activated as readily by glucan greater than one micron in diameter because the receptor size on corresponding cells and molecules that accept the glucan is generally about one micron in size.

The re-aggregation and resistance to de-aggregation is accentuated in environments with low pH such as a human digestive tract, such as at a pH of less than 1.0. As the glucan re-aggregates into particles of greater than one micron in diameter, it appears to pass through an animal or human digestive system without substantially complete absorption.

Accordingly, the art field has searched for a reliable method to produce substantially purified glucan aggregates that remain substantially in a particle size of one micron in diameter or less throughout preparation and packaging without re-aggregation.

SUMMARY OF THE INVENTION

The present invention generally relates to the preparation of a dry glucan product that substantially de-aggregates upon hydration into particles of 1 micron or less.

This summary is not intended to be a limitation with respect to the features of the invention as claimed, and this and other objects can be more readily observed and understood in the detailed description of the preferred embodiment and the claims that follow.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

GENERAL DESCRIPTION AND PREFERRED MODE FOR CARRYING OUT THE INVENTION

Figure 1:
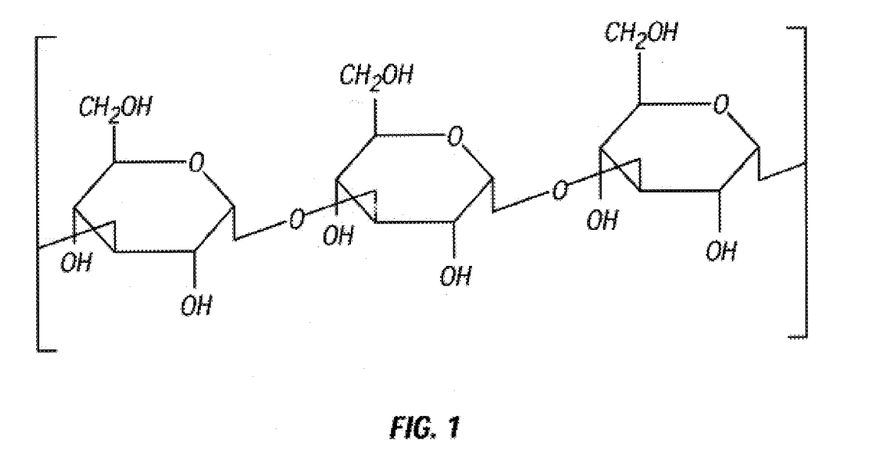
FIG. 1 is a diagrammatic representation of a unit of beta linked glucopyranose.

Referring now to FIG. 1, an illustration of a unit of a beta (1,3) glucan. Generally, under the present method of preparation the resulting size of the glucan polysaccharide can be of any number "n" to produce varying chain lengths.

The glucan containing composition may be made by any means common in the art. A general method of manufacture of a glucan is set out as follows from a second specific procedure is described in the Carbohydrate Research article by N. Di Luzio et al as previously referenced:

1. 0.45 kg of dry Saccharomyces cerevisiae is dispersed in 3.5 L of 0.75 (3%) NaOH 2. Heat to boiling with direct heat. Let stand overnight: decant and discard brown supernatant.

3. Repeat the NaOH digestion (2×)

4. Add 3.5 L of 2.45M HCl to residue. Heat to boiling with direct heat.

5. Let stand overnight: decant and discard light brown supernatant.

6. Repeat the HCl digestion twice, using 1.75M and then 0.94M.

7. To the residue add 2 L distilled water under sufficient pressure to effect mixing.

8. Heat to boiling on hot plate. Let stand overnight: decant and discard supernatant.

9. Repeat the water wash until the residue becomes white and flocculent (20×).

10. To the residue add 1.5 L of abs EtOH. Heat to boiling with direct heat.

11. Let stand overnight: decant and discard yellowish supernatant.

12. Repeat the EtOH extraction until the supernatant becomes colorless (3–4 times).

13. Add 2 L distilled water to the residue under sufficient pressure to achieve mixing.

14. Heat to boiling with direct heat. Let stand overnight: decant and discard supernatant.

15. Repeat the water wash (3×).

16. Pour the washed particulate glucan through a fine silk screen.

17. Shell freeze and lyophilize to dryness.

18. Yield: 2% glucan by volume.

The aforementioned method of preparation of a glucan containing composition is general and it will be understood by those of skill in the art that variations on the aforementioned method will still lie within the scope of the present invention. Further, the resulting glucan containing composition may be of varying compositions and percentages of glucan. In a most preferred embodiment the resulting glucan solution is about 2% to 5% glucan by volume.

The glucan prepared above exists predominantly in the globule form. As noted previously, it is desirable to reduce the globule size to predominantly less than one micron in diameter.

Reducing the size of the glucan globule to predominantly less than one micron in diameter may be achieved by sonication of a glucan containing composition. In a preferred embodiment a glucan containing composition is first hydrated for a period of at least about twelve hours. In a most preferred embodiment the glucan containing composition is hydrated overnight in water.

Then, in a preferred embodiment, a portion of the glucan may be containerized prior to sonication. A preferred embodiment uses an ordinary tray or dish as a container. The container may then be placed in an ultrasonic water bath to dissociate the large globules of glucan. Experimental results have indicated that the size of the container has a direct effect on results of sonication. In a preferred embodiment, a container is selected that allows for 10 to 50 mm space between the container walls and a sonicator probe. However, various other embodiments of the present invention may utilize any variety of containers of varying size.

In a preferred sonication step, the container is sonicated for three-twelve (12) minute intervals with short twelve (12) minute breaks between cycles. In a most preferred embodiment, the container is sonicated for one (1)- twelve (12) minute cycle in an ice bath for cooling the glucan as it is heated during sonication. The short breaks in the cycling are used because the sonication of the glucan generates a considerable amount of heat and cooling of the glucan containing composition is necessary to prevent excessive heating and denaturing or degradation of the product.

In a most preferred embodiment a bench-top sonicator of choice is a BioLogics 300 V/T Sonic Dismembrator. A preferred embodiment utilizes the settings of the sonicator at 80% power and 80% duty cycle for 12 minute cycles with the container in an ice bath. A preferred probe for use is a 19 mm (¾") diameter titanium probe. However, other probes may be utilized and still be within the scope of the present invention. A preferred power setting for a one (1) duty cycle sonication is 192 watts for 48 seconds with a 12 second pause at an ultrasonic output of 20 kilocylcles per second. Other power settings may be used for sonication, however, the time and number of duty cycles may vary accordingly Experimental studies have shown that excessive sonication of the glucan creates heat that may denature the glucan and shortened life of the sonic probe. Accordingly, care should be taken not to over sonicate the glucan and to provide a sufficient time in between cycles to allow the probe to cool. The process of the most preferred embodiment will dissociate substantially all of the glucan globules to particles one micron in diameter or less.

For larger volume small particle glucan production operations a commercially available sonic dismembrator may be used. Experimental results have shown that the BioLogics, Inc. sonic dismembrator, with a continuous flow chamber, indicated that about 95% of a fully hydrated glucan may be dissociated after one (1) to three (3) treatments at a flow rate of 16 ml/min and 80% power with 12 minutes per treatment. Preferred embodiments of this method utilize one treatment to fully disassociate the glucan.

After sonication, the glucan remains in suspension in an aqueous state for a sufficient period of time for applications requiring suspension of the glucan such as pharmacological applications; including both pharmaceutical and pharmacological applications, nutritional applications, and supplementary applications for animals, humans and plants.

In a preferred embodiment, before the initial sonication of the glucan, a percentage gelatin solution, or similar solution, may be added to the glucan solution. In a most preferred embodiment the percentage gelatin solution is a 5% gelatin solution in de-ionized water. In a most preferred embodiment the 5% glucan solution is diluted to about a 2% glucan solution with water and the 5% gelatin solution. Then the glucan may be sonicated as indicated above. In this preferred embodiment the glucan may be utilized wet or dry. A most preferred method for drying the glucan of this embodiment is lyophilizing or freeze drying. A preferred method of freeze drying utilizes an ultralow freezer to freeze the glucan at −80 degrees centigrade. The time required to freeze dry the glucan varies depending upon the amount of glucan, but generally will take between 1 to 2 hours. However, the length of time to freeze dry may vary. The resulting glucan containing composition will dry into a friable, paper-like constituency, and upon re-hydration the glucan will disassociate into substantially 1 micron in diameter particles.

In another preferred embodiment the wet, gelatinized glucan may be added to a capsule and freeze dried. Upon re-hydration the glucan will de-aggregate into predominantly 1 micron or less in diameter glucan.

Figure 3A:
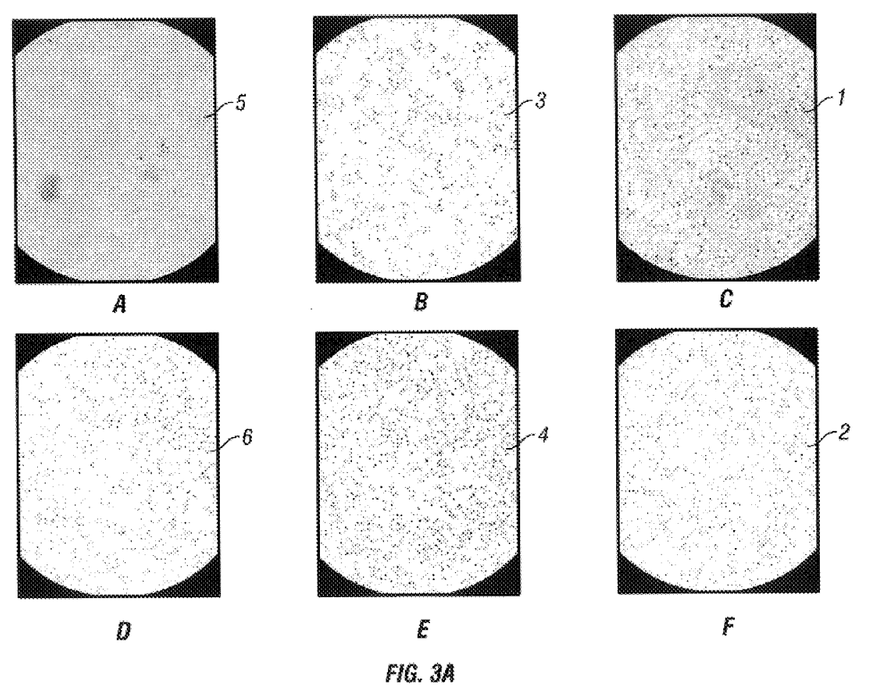
FIG. 3a is an illustration of glucan particles and the effects of various methods of preparation.
Figure 3B:
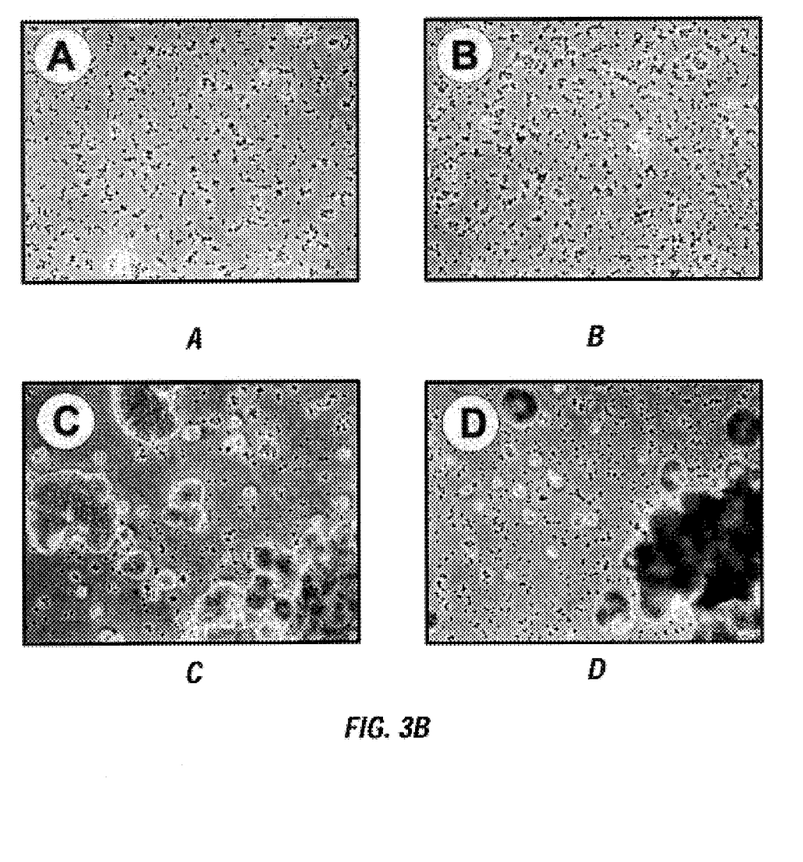
FIG. 3b is an illustration of a microscopic examination of the effects of dehydration on sonicated glucan.

In another preferred embodiment, a sugar is added to a sonicated glucan, without the gelatin. In a most preferred embodiment the sugar is maltodextrose. However, other embodiments of the present invention may utilize both a gelatin and a sugar in the glucan. The resulting glucan containing composition may then placed in a commercially available spray drier for application. A preferred sprayer is the Spray Drying Systems spray drier. A fine, non-aggregated powder, is formed from the spraying. The resulting glucan containing composition, existing substantially as a powder, may then be loaded into capsules, pills or other containers. The powder may also be stored and later re-hydrated for future use.

The preferred spray dryer utilizes an inlet air temperature of 110 to 170 degrees Centigrade, an outlet air temperature of 90 to 120 degrees Centigrade and a feed solids composition of 0.5 to 1.0 percent. However, other settings and spray dryers may be used and be within the scope of the present invention varying the quality of the sprayed glucan. In fact, other settings may be required when using a different spray dryer. The preferred spray dryer produces a finely sprayed glucan powder that does not re-aggregate into glucan globules.

The following examples do not limit the scope of Applicant's invention, but serve as an explanatory tool in the many advantages of Applicant's invention.

EXAMPLE 1

FIG. 2 illustrates the morphology of beta-glucan-containing globules of various sizes commonly available on the market. These glucan-containing globules are illustrated in a hydrated state. In the hydrated state, glucan aggregates into globules 7. These glucan globules consist of numerous individual and linked beta glucans. Further, as the glucan aggregates, the size of the glucan globule becomes greater than 1 micrometer.

Several methods have existed in the art to disassociate globules 7, but most have not proven effective without harsh treatment to the glucan that often results in chemical changes to the glucan or the loss of its beneficial effects. For example, common methods employed to disassociate the globules include grinding and vortexing. However, none of these methods have proven reliable and often do not consistently produce a small particle glucan. Additionally, the hydration of the glucan causes the glucan to re-aggregate into glucan globules 7. Accordingly, the art field has sought a method of producing an aqueous glucan that is substantially disassociated from the globule glucan.

As stated in the background, it is more advantageous to have a small beta glucan globule that resists aggregation into large globules for a sufficient time for application. Therefore, the art field has searched for a reliable method for producing small particle size glucan that resists aggregation into a large glucan globular.

EXAMPLE 2

FIG. 3, an illustration of glucan particle size and the effects of various methods of preparation, demonstrates the reduction in size of the glucan globules upon sonication.

Slide C is raw glucan at about 200 times magnification. Globule 1 of raw, untreated glucan may be observed. Slide F is a sample of raw glucan at about 200 times magnification that has been ground to a fine ground particle size of the glucan globule 2. It may be observed the glucan globule 2 is generally of smaller size than the glucan globule 1 of Slide C.

Referring now to Slide B of FIG. 3, Slide B is a sample of raw glucan that has been sonicated with a BioLogics V/T Sonic Dismembrator at 80% power and 80% duty cycle for 12 minute cycles in an ice bath, viewed at about 400 times magnification. It may be observed that globule 3 is generally of a smaller globule size than globule 1. It may also be observed that globule 3 is generally more dispersed than globule 1.

Another improvement may be shown in Slide E of FIG. 3, Slide E is a sample of ground glucan that has been sonicated with a BioLogics 300 V/T Sonic Dismembrator at 80% power and 80% duty cycle for 12 minute cycles in an ice bath, viewed at about 400 times magnification. It may be observed that globule 4 is generally of a smaller globule size than globule 1 or globule 2. It may also be observed that globule 4 is generally more dispersed than globule 1 or globule 2.

Another improvement in the reduction of the globule size may be shown in Slide A of FIG. 3. Slide A is a sample of ground glucan that has been sonicated with a BioLogics 300 V/T Sonic Dismembrator at 80% power and 80% duty cycle for 12 minute cycles in an ice bath, dried and then rehydrated viewed at about 400 times magnification. It may be observed that globule 5 is generally of a smaller globule size than globule 1 or globule 2. It may also be observed that the globule 5 is generally more dispersed than globule 1 or globule 2. It may also be observed that the glucan rehydrated after being dried to contain globule 5 that has a globule size generally less than one micron.

Comparable results to that of Slide A were obtained in Slide D of FIG. 3. Slide D is a sample of ground glucan that has been sonicated with a BioLogics V/T Sonic Dismembrator at 80% power and 80% duty cycle for 12 minute cycles in an ice bath, dried and then rehydrated viewed at about 400 times magnification. It may be observed that the globule 6 is generally of a smaller globule size than globule 2 or globule 1.

The experimental results indicate that a small particle glucan of substantially one micron or less in particle size may be obtained by sonication without the necessity of grinding, thereby reducing the amount of time required to produce a small particle size glucan.

FIG. 3*b*, an illustration of a microscopic examination of the effects of dehydration on sonicated glucan, is illustrative of the preferred results obtained after sonication of a glucan. Slide A is a glucan suspension after subjection to three sonication treatments at a flow rate of 16 ml/min and 80% power. The results were taken after drying the glucan and then rehydrating through vortex mixing. Slide B is a glucan suspension after subjection to three sonication treatments at a flow rate of 16 ml/min and 80% power. The results were taken after drying then rehydrated by grinding with a mortar and pestle in de-ionized water. Slide C is a glucan, not sonicated, only suspended in a de-ionized water solution by vortex mixing. Slide D is a glucan, not sonicated, only suspended in de-ionized water after grinding by a mortar and pestle.

As may be observed from FIG. 3b, an illustration of a microscopic examination of the effects of dehydration on sonicated glucan, the resulting glucan is most finely separated in Slide A and in Slide B after both sonication and vortex mixing. Slide C is not finely separated and results in large globules because no sonication was utilized. Slide D results in a more finely separated glucan than Slide C after grinding, but still results in large glucan globules in the absence of sonication.

Figure 3C:
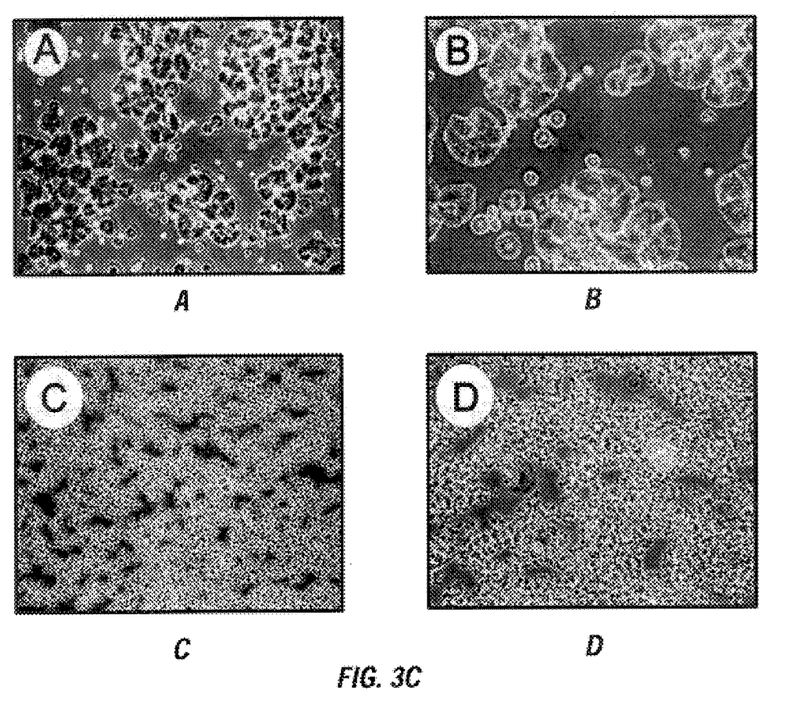
FIG. 3c is an illustration of a microscopic examination of the effects of sonic energy on glucan globules.

FIG. 3c, an illustration of a microscopic examination of the effects of sonication on glucan globules, is demonstrative of the reduction in particle size of glucan globules after sonication. Slide A is a 2% glucan suspension in de-ionized water after vortex mixing viewed at 10×. Slide B is the identical solution of Slide A at 20× magnification. Slide C is Slide A after three treatments of sonication at 16 ml/min at 80% power viewed at 10× magnification. Slide D is the identical solution of Slide C viewed at 40× magnification.

As may be observed from FIG. 3c, an illustration of a microscopic examination of the effects of sonic energy on glucan globules, the glucan globules are reduced to small particle size glucan after sonication.

EXAMPLE 3

Figure 2:
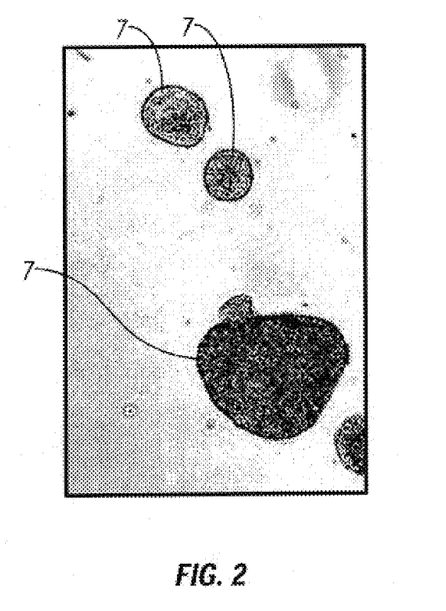
FIG. 2 is an illustration of glucan particles in a naturally hydrated state.
Figure 4:
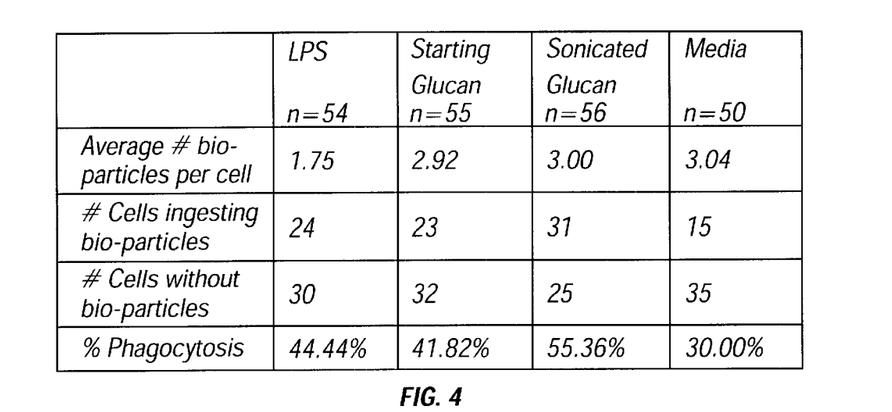
FIG. 4 is an illustration of tabular results of a phagocytosis assay.

FIG. 4, an illustration of a phagocytosis assay, demonstrates the enhanced phagocytosis of the small particle size glucan. The data for FIG. 4, an illustration of a phagocytosis assay, was generated from an assay in which phagocytosis was measured utilizing fluorescent bio-particles. This experiment was conducted to determine the glucan induced macrophage activity. An assay was performed using the ground glucan from FIG. 2, predominantly particle size 1–100 micron in diameter, and another assay was performed using the sonicated beta glucan from FIG. 3, Slide D, predominantly 1 micron or less in diameter, particle size glucan. A bacterium, *Staphylococcus aureus*, was labeled with a fluorescent marker, fluorescein isothiocyanate (FITC). This dye was chosen because when viewed using fluorescent microscopy the dye emits a yellow-green light.

The labeled cells were mixed with macrophages for about 20 minutes. After incubation, the assays were rinsed with Trypan Blue, pH 4.4. The acidic solution quenched the fluorescence of FITC, causing the labeled bacterium to no longer emit the yellow-green light. However, the bacterium that have been phagocytised are protected from the quenching and emit the yellow-green light when viewed under the fluorescent microscope.

A comparison of the total number of bacterium ingested in the macrophages of the untreated glucan and treated glucan demonstrate an improved percentage of phagocytosis. As demonstrated by FIG. 4, the average number of bio-particles per cell changed from 2.92 for the raw untreated glucan to 3.00 for the treated glucan.

However, a comparison of the total number of macrophage cells ingesting the bio-particles demonstrated an increase in activity from the untreated macrophage to the treated macrophage. When the total number of macrophages were compared with the total number of macrophages ingesting the bacterium, the percentage phagocytosis, was found to be increased from 41.82 percent for the raw untreated glucan to 55.36 percent for the treated glucan. The increased percentage phagocytosis indicates an increase in the activity of the macrophage.

This example was performed with macrophage-like tumor cell lines J774A.1 and P388D1. These cells were allowed to grow on 4 chambered LabTek Tissue Culture Slides to subconfluency. The cells were then exposed to lipopolysaccharide (LPS 50 $\mu$g/ml) from *Escherichia coli* 0111:B4, a known activator of macrophages, a solution of glucan globules (100 $\mu$g/ml), a solution of DSM-glucan (100 $\mu$g/ml) or media. After 1 hour incubation, the stimulant was removed and replaced with growth media. Twenty-four hours post-stimulation the cells were evaluated for activation and a phagocytic index calculated as is demonstrated in FIG. 4.

The greater percentage phagocytosis demonstrates the enhanced activity of the macrophage and the small particle size glucan's ability to activate the immune system.

EXAMPLE 4

Figure 5:
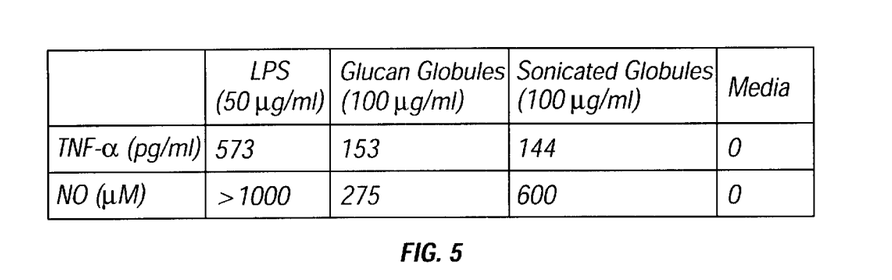
FIG. 5 is an illustration of tabular results for Nitric Oxide production of a glucan activated macrophage.

FIG. 5, an illustration of tabular results for Nitric Oxide production of glucan activated macrophage, demonstrates the enhanced production of Nitric Oxide, NO, from the untreated glucan to the sonicated glucan. The data demonstrates a factor of two increase in the production of NO from comparison of the untreated glucan to the treated glucan; from 275 $\mu$M to 600 $\mu$M. The measurement of NO production is indicative of an oxidative burst that kills and/or destroys the ingested microbes and/or particles by the macrophage.

This experiment was performed by measuring NO by antigen capture enzyme immunoassay. Macrophages were stimulated for 1 hour with LPS (50 $\mu$g/ml), glucan globules (100 $\mu$g/ml), sonicated glucan (100 $\mu$g/ml, or media. After stimulation the stimulant was replaced with growth media. Twenty-four hours post-stimulation the culture supernatant was assayed for NO production.

The greater generation and/or production of NO demonstrates the enhanced activity of the macrophage with a small particle size glucan which is indicative of an activity level of an immune system.

While a single method and embodiment has bees shown, illustrated and described, various other embodiments may be utilized and be within the scope of the present invention.

What is claimed is:

1. A method for preparing a small particle size glucan for improved immunological response through enhanced activation of a macrophages and freeze drying the glucan such that re-hydration of the glucan disassociates the glucan, comprising the steps of:

obtaining a polysaccharide composition comprising a glucan containing composition;

hydrating the glucan containing composition with a liquid;

disrupting the glucan;

adding a gelatin solution to the hydrated glucan; and, freeze drying the glucan.

2. The method of claim 1 wherein the gelatin solution is two percent.

3. The method of claim 1 further comprising the step of drying the hydrated glucan whereby the glucan settles.

4. The method of claim 3 further comprising the step of grinding the glucan.

5. The method of claim 3 further comprising the step of rehydrating the glucan whereby a portion of the glucan is dissociated into particles of about 1 micron in diameter.

6. The method of claim 1 further comprising the step of drying the hydrated glucan.

7. The method of claim 5 further comprising the step of hydrating the dried glucan with a liquid whereby a portion of the glucan is one micron in diameter glucan.

8. The method of claim 1 wherein the glucan is composed of a yeast cell wall extract.

9. The method of claim 1 wherein the liquid is water.

10. The method of claim 1 wherein the glucan is substantially glucan selected from the group comprising beta-(1,3)-glucan and beta-(1,6)-glucan.

11. The method of claim 1 wherein the disrupting is accomplished by sonicating the glucan.

12. An improved method of producing a glucan in a solid that when re-hydrated substantially de-aggregates into glucan particles of less than one micron comprising the steps of:

purifying a yeast cell wall extract such that the yeast cell wall extract is a portion a glucan;

hydrating the extract with a liquid to form a glucan solution;

disrupting the glucan solution whereby the glucan de-aggregates substantially to a glucan of about one micron in diameter; and, freeze drying the glucan whereby a substantially solid sheet of glucan is produced whereby upon re-hydration with a liquid the glucan substantially de-aggregates into about one micron in diameter particle size glucan.

13. The method of claim 12 further comprising the step of adding a gelatin solution to the glucan before freeze drying.

14. The method of claim 12 wherein the liquid for re-hydration is water.

15. The method of claim 14 wherein the glucan is substantially glucan selected from the group comprising beta-(1,3)-glucan and beta-(1,6)-glucan.

16. The method of claim 14 wherein the gelatin solution is two percent gelatin by volume.

17. A method of producing a glucan solid that when re-hydrated de-aggregates into glucan particles substantially less than one micron in diameter comprising the steps of:

obtaining a glucan containing composition, the glucan containing composition substantially glucan selected from the group consisting of beta (1,3)-glucan and beta (1,6)-glucan;

hydrating the glucan such that the glucan containing composition is hydrated to five percent glucan by volume;

adding a gelatin solution such that the glucan containing composition is diluted to two percent glucan containing composition by volume;

disrupting the glucan containing composition; and, freeze drying the glucan containing composition.

18. The method of claim 17 wherein the gelatin solution is five percent gelatin by volume.

19. The method of claim 18 wherein the disrupting the glucan containing composition is by sonication of the glucan containing composition.

* * * * *